United States Patent [19]

Lee et al.

[11] Patent Number: 5,064,823
[45] Date of Patent: Nov. 12, 1991

[54] PENTACYCLIC TRITERPENOID COMPOUNDS AS TOPOISOMERASE INHIBITORS OR CELL DIFFERENTIATION INDUCERS

[75] Inventors: Yue-Wei Lee, Research Triangle Park, N.C.; Qi-Cheng Fang, Beijing, Taiwan; Zhen-Guo Wang; De-Hua Li, both of Jilin, Taiwan; C. E. Cook, Research Trinagle Park, N.C.

[73] Assignee: Research Triangle Institute, Research Triangle, N.C.

[21] Appl. No.: 517,176

[22] Filed: May 1, 1990

Related U.S. Application Data

[63] Continuation of Ser. No. 235,903, Aug. 24, 1988, abandoned.

[51] Int. Cl.[5] .................... A61K 31/43; A01N 63/00
[52] U.S. Cl. .................. 514/198; 424/195.1
[58] Field of Search ............ 514/198; 424/180, 195.1

[56] References Cited

U.S. PATENT DOCUMENTS 4,501,734  2/1985  Tanaka et al. .................. 514/198

Primary Examiner—Nathan M. Nutter
Attorney, Agent, or Firm—Oblon, Spivak, McCelland, Maier & Neustadt

[57] ABSTRACT

Pentacyclic triterpenoid compounds such as α boswelic acid and its acetate, β-boswellic acid and its acetate, which have an inhibitory effect on topoisomerase I and topoisomerase II, are disclosed. Compositions based on the pentacyclic triterpenoid compounds which can be used to treat various cancers in mammals are also disclosed.

14 Claims, 6 Drawing Sheets

| Column No. | DNA | Topoisomerase I Enzyme (units) | Drug Concentration (μM) | Activity |
|---|---|---|---|---|
| A | pBR322 | 0 | 0 | — |
| B | " | 0.75 | 0 | — |
| C | " | 1.5 | 0 | — |
| D | " | 3.0 | 0 | — |
| E | pBR322 | 3.0 | Camptothecin (1.6 μM) | — |
| F | " | 3.0 | Camptothecin (4.0 μM) | — |
| G | " | 3.0 | Camptothecin (10 μM) | ++ |
| H | pBR322 | 3.0 | A-1 (1.6 μM) | — |
| I | " | 3.0 | A-1 (4.0 μM) | + |
| J | " | 3.0 | A-1 (10.0 μM) | ++ |
| K | pBR322 | 3.0 | B-1 (1.6 μM) | — |
| L | " | 3.0 | B-1 (4.0 μM) | — |
| M | " | 3.0 | B-1 (10.0 μM) | ++ |

| Column No. | DNA | Topoisomerase II Enzyme (units) | Drug Concentration (μM) | Activity |
|---|---|---|---|---|
| A | P4 (knotted) | 0 | 0 | — |
| B | " | 0.75 | 0 | — |
| C | " | 1.5 | 0 | — |
| D | " | 3.0 | 0 | — |
| E | P4 (knotted) | 3.0 | VP-16 (25) | — |
| F | " | 3.0 | VP-16 (50) | — |
| G | " | 3.0 | VP-16 (100) | ++ |
| H | P4 (knotted) | 3.0 | A-1 (0.625) | — |
| I | " | 3.0 | A-1 (2.5) | — |
| J | " | 3.0 | A-1 (10) | ++ |
| K | P4 (knotted) | 3.0 | B-1 (0.625) | — |
| L | " | 3.0 | B-1 (2.5) | — |
| M | " | 3.0 | B-1 (10) | ++ |

PENTACYCLIC TRITERPENOID COMPOUNDS AS TOPOISOMERASE INHIBITORS OR CELL DIFFERENTIATION INDUCERS

This is a continuation of application Ser. No. 07/235,903, filed on Aug. 24, 1988, abandoned.

BACKGROUND OF THE INVENTION

FIELD OF THE INVENTION

This invention relates generally to pentacyclic triterpenoid compounds such as α-boswellic acid acetate, β-boswellic acid acetate and their analogs which possess topoisomerase inhibitory, cell differentiation inducing and/or anti-cancer activities.

DISCUSSION OF THE BACKGROUND

1. Introduction

DNA topoisomerases I and II are nuclear enzymes which can mediate structural transitions in DNA and chromatin by their ability to break and rejoin single or double strands of DNA, respectively. These enzymes can catalyze many types of interconversions between DNA topological isomers. Examples are catenation and decatenation and knotting and unknotting. DNA topoisomerases have been found to affect a number of vital biological functions including replication, transcription, recombination and repair (Gellert, M., Ann. Rev. Biochem., 50, 879-910 (1981); Wang, J. C., Ann. Rev. Biochem, 54, 665-695 (1985); Cozzarelli, N. R., Cell, 22, 327-328 (1980); and Liu, L. F., Crit. Rev. Biochem., 15, 1-24 (1983)).

Topoisomerases have been isolated from a wide variety of biological sources, such as bacteria, *E. coli* and *M. luteus;* bacteriophage, T4; yeast, *Saccharomyces;* insects, *Drosophila;* amphibians, *Xenopus;* and mammals. Hela cells, calf thymus, mouse leukemia cells and human leukemic cells (Miller, K. G., et al., J. Biol. Chem. 256, 9334 (1987); Pommier, Y., et al., Biochem. 24, 6410 (1985)).

In the bacterium *E. coli,* a new type I topoisomerase, DNA topoisomerase III, has been found. This enzyme, similar to the other type I enzymes, relaxes negatively supercoiled DNA (Wang, 1985).

One important feature of the mechanism of topoisomerases is their ability to form a covalent protein-DNA complex during the reaction. In the case of topoisomerase I, this involves a phosphotyrosyl bond between the enzyme and the 3' terminus of the break site, while in the case of topoisomerase II, the phosphotyrosyl bonds formed with the 5' termini. It is clear that through these actions on DNA topology and the breaking and rejoining of DNA strands, the topoisomerases are involved in a diverse number of vital cellular processes (Vosberg, H. P., Current Topics in Microbiology and Immunology, p. 19, SpringerVerlag: Berlin (1985); Wang, J. C., Ann. Rev. Biochem, 54, 665-695. (1985)).

Thus, the development of chemical agents capable of modulating the enzyme activity of topoisomerases would have considerable value for manipulation of gene expression and chemotherapeutic intervention of cancer.

2. DNA Topoisomerases in Cancer Chemotherapy

Since 1980, DNA topoisomerases have emerged as target enzymes of considerable promise in cancer chemotherapy. Previously, antitumor drugs such as doxorubicin, daunorubicin, amsacine (m-AMSA) and mitoxantrone were believed to work by intercalating DNA, thereby blocking the orderly progression of DNA and RNA polymerases. However, this notion did not fully account for potency differences between various intercalating agents and did not account for the production of DNA breakage when cells were exposed to these agents. In addition, anticancer drugs such as epipodophyllotoxin (EPP), etoposide and teniposide do not intercalate into DNA. It is now believed that these drugs actually kill cells via their interaction with the nuclear enzyme DNA topoisomerases (Tewey, K. M., et al., J. of Biol. Chem., 259, 9182 (1984a); Tewey, K. M., et al.,.Science, 226, 466 (1984b); Rowe, T. C., et al., Cancer Res., 46, 2021 (1986)).

Fast growing evidence clearly suggests that topoisomerases I and II each have an important function in DNA replication and genetic processes via the formation of the "cleavable complex". Thus, inhibition of topoisomerases or stabilization of the topoisomerase-DNA "cleavable complex" may be interpreted as a form of DNA damage in the cell. Consequently, this damage induces the cell's effort to process or repair the cleavable complex and therefore activates the proteases whose expression is lethal and ultimately leads to the cells' death (Liu, L., National Cancer Institute Monographs (1987)).

TOPOISOMERASE I INHIBITORS

Topoisomerase I has become a target enzyme of considerable interest in recent drug development. For instance, camptothecin (CMT) has been shown to inhibit RNA and DNA synthesis in a variety of animal and human tumor cell lines *in vitro* (Bosman, H. B., Biochem. Biophys. Res. Commun., 41, 1412 (1970); Horwitz, M. S. and Horwitz, S. B., Biochem. Biophys. Res. Commun., 45, 723 (1971); Kessel, D., et al., Biochim. Biophys. Acta., 269, 210 (1972); Li, L. H., et al., Cancer Res., 32, 2643 (1972); Bhuyan, B. K., et al., Cancer Res., 33, 888 (1973); Drewinko, B., et.al., Cancer Res., 34, 747 (1974)) and *in vivo* (Gallo, R. C., et al., J. National Cancer Institute, 46, 789 (1971); Neil, G. L., et al., Cancer Res., 33, 895 (1973). The observations of a good correlation between inhibition of nucleic acid synthesis, DNA strand breakage and *in vivo* antitumor activity have led to the conclusion that effect on DNA was a primary determinant of cytotoxicity.

Recent interest in the possible use of CMT derivatives with improved therapeutic ratios has led to more extensive studies of their mode of cytotoxicity. Hsiang et al. (J. Biol. Chem., 260, 14873 (1985)) have reported that CMT blocks the rejoining step of the breakage-reunion reaction of topoisomerase I with DNA. CMT, which does not cleave purified DNA (Horwitz, M. S. and Horwitz, S. B., Biochem. Biophys. Res. Commun., 45, 723 (1971); Hsiang, Y. H., et al., J. Biol. Chem., 260, 14873 (1985)), induced sitespecific cleavage of DNA in the presence of purified mammalian topoisomerase I (Castora, F. J. and Kelley, W. G., Proc. Natl. Acad. Sci. 83, 1680 (1986)) which was linked to the 3' end of the broken DNA strands (Hsiang, Y. H., et al., J. Biol. Chem., 260, 14873 (1985)). Induction of strand breakage was immediate and reversible upon removal of the drug or incubation with 0.5 M salt. CMT did not intercalate into DNA, single or double stranded. It induced no DNA cleavage via purified mammalian topoisomerase II, nor did it inhibit the enzyme's catalytic activity (Hsiang, Y. H., et al., J. Biol. Chem., 260, 14873 (1985)). These data clearly indicate that CMT specifically inhibits mammalian topoisomerase I, and its cytotoxic effects may be explained by stabilization of a cleavable complex between enzyme and DNA, resulting in inhibition of nucleic acid synthesis and induction of DNA strand breaks.

TEPOISOMERASE II INHIBITORS

Recently, a number of clinically active antitumor drugs have been shown to enhance DNA cleavage by purified eukaryotic DNA topoisomerase II (Nelson, E. M., et al., Proc. Natl. Acad. Sci. USA, 81, 1361 (1984); Tewey, K. M., et al., J. of Biol. Chem., 259, 9182 (1984a); Tewey, K. M., et al., Science, 226, 466 (1984b); Ross, W., et al., Cancer Res., 44, 5857 (1984); Minocha, A., et al., Biochem. Biophys. Res. Commun., 122, 165 (1984)). For example, the intercalative aminoacridine derivative 4'-(9-acridinyl-amino)methansulfon-m-aniside (m-AMSA) markedly stimulates the breakage of DNA by mammalian DNA topoisomerase II at a concentration of 20 $\mu$g/mL (Nelson, E. M., et al.,.Proc. Natl. Acad. Sci. USA, 81, 1361 (1984); Rowe, T. C., et al., Cancer Res., 46, 2021 (198)). Other intercalative and nonintercalative antitumor drugs including adriamycin, 5-iminodaunorubicin, ellipticine, 2-methyl-9-hydroxyellipticine and epipodophyllotoxins, VP-16 and VM-25, function similarly in vitro (Ross, W., et al., Cancer Res., 44, 5857 (1984); Minocha, A., et al., Biochem. Biophys. Res. Commun., 122, 165 (1984); Tewey, K. M., et al., J. of Biol. Chem., 259, 9182 (1984a); Tewey, K. M., et al., Science, 226, 466 (1984b); Chen, G. L.,.et al., J. of Biol. Chem., 259, 13560 (1984)). This topoisomerase-mediated DNA breakage was directly demonstrated by Liu's group, who found that the drug caused the enzyme to be covalently linked to the 5' terminus of the break site upon denaturation.

Structure-activity relationship studies of closely related drug congeners provided strong support that both intercalating agents and EPP interact directly with the enzyme and potentiate the cleavable-complex formation (Silber, R., et al., Natl. Cancer Institute Monographs 4, 111 (1987)). Moreover, excellent correlations were observed between cytotoxicity and potency with respect to cleavable complex formation in vivo and in vitro (Rowe, T. C., et al., Cancer Res., 46, 2021 (1986); Long, B. H., et al., Biochemistry, 23, 1183 (1984); Levin, M., et al., Cancer Res., 41, 1006 (1981); Zwelling L. A., et al., Biochemistry, 20, 6553 (1981); Nelson, E. M., et al., Proc. Natl. Acad. Sci. USA, 81, 1361 (1984)).

These topoisomerase-mediated DNA breaks are postulated to be responsible for the drug's cytotoxicity.

3. Cell Differentiation in Cancer Chemotherapy

Cancer can be considered a disorder of cell differentiation (Pierce, G., et al., Cancer, A Problem of Developmental Biology, Englewood Cliffs, Prentice Hall, 1978; Greaves, M. F., J. Cell Physiol., 1, 113-125 (1982)), which is readily illustrated by the hematologic neoplasms. Oncogenic conversion, defined as the arrest of differentiation without loss of proliferative capacity can occur at any of the intermediate maturation steps. Consequently, the maturation-arrested cells continue to proliferate, a population of immature "cancer" cells emerges and gives rise to adverse clinical manifestations (Bloch, A., Cancer Treatment Reports, 68, 199 (1984)).

Under normal conditions, proliferation and maturation are regulated by growth factors (GF) and differentiation factors (DF), respectively. The neoplastic cell can be derived from events that alter the cell's sensitivity to these factors. These changes may entail increased sensitivity to GF, decreased responsiveness to DF, decreased elaboration of DF by the host and endogenous production of GF by the neoplastic cell itself (Todaro, G. I., Fed. Proc., 41, 2987 (1982)).

Almost all clinically effective anticancer agents are inhibitors of DNA synthesis or transcription (Bloch, A., Purine and Pyrimidine Analogs in Cancer Chemotherapy in *New Leads in Cancer Therapeutics* (E. Mihich. ed.), Boston, G. K. Hall and Co., 1981, pp. 65-72). The notion that the antitumor activity results from the ability of DNA-targeted agents to induce the maturation of sensitive cancer cells past the stage of oncogenic differentiation arrest, thereby removing their capacity for unlimited proliferation, is implicated in recent studies (Takeda, K., et al., Cancer Res., 42, 5152-5158 (1982)). These studies clearly demonstrate that only DNA-specific inhibitors such as daunorubicin or cytarabine are capable of effectively inducing the differentiation of various myeloid leukemic cell lines.

4. Boswellic Acids

Frankincense (Olibanum), a costly resin produced by members of the genus Burseraceae, has been widely used in perfumery, for religious purposes and as a folk medicine in the treatment of several diseases, including inflammation and arthritis [Chinese Herbal Dictionary, 1, 1379-1381 (1977); Yadav, D. S., et al., Abstracts of Papers Presented at the Scientific Session "Medical Chemistry", Indian Pharmaceutical Congress, Bangalure, February, 1985]. Results of chemical examination have shown it to contain a number of compounds, including $\alpha$-boswellic acid, $\beta$-boswellic acid, acetyl $\alpha$-boswellic acid, other triterpenoid carboxylic acids, and macrocyclic diterpenoids such as incensole, incensole oxide and isoincensole oxide (Winterstein, A., et al., Physiol. Chem., 208, 9 (1932); Chem. Abstr., 26, 4321 (1932); Simpson, J. C. E., et al., J. Chem. Soc., 686 (1938); Beton, J. L., et al., J. Chem. Soc., 2904 (1956); Corsano, S., et al., Tetrahedron, 23, 1977 (1967); Nicoletti, R. and Forcellese, M. L., Tetrahedron, 24, 6519 (1968); Nicoletti, R., Forcellese, M. L., and Petresi, U., Tetrahedron, 28, 325 (1972); Nicoletti, R., Santarelli, C., and Forcellese, M. L., Tetrahedron Lett., 3783 (1973)). It has now been reported that its antiinflammatory and antiarthritic activities are due to the presence of $\beta$-boswellic acid and other related triterpenoid carboxylic acids (Yadav, D. S., et al., Abstracts of Papers Presented at the Scientific Session "Medical Chemistry", Indian Pharmaceutical Congress, Bangalure, February, 1985). In spite of these activities, up to now, no one has recognized that a triterpenoid compound could inhibit any topoisomerase or cause cell differentiation.

Accordingly, one object of the present invention is to provide compositions which are capable of inhibiting topoisomerase I in vitro and in vivo.

Another object of the present invention to provide compositions which are capable of inhibiting topoisomerase II in vitro and in vivo.

Another object of the present invention is to provide compositions which are capable of inducing cellular differentiation, particularly differentiation of cells past the stage of oncogenic differentiation.

It is yet another object of the present invention to provide a method of inhibiting topoisomerase I in vitro and in vivo.

Another object of the present invention is to provide a method for inhibiting topoisomerase II in vitro and in vivo.

Yet another object of the present invention is to provide a method for inducing cellular differentiation past the stage of oncogenic differentiation.

Another object of the present invention is to provide compositions for treating various cancers.

Another object of the present invention is to provide a method for treating various cancers.

These and other objects of the present invention as will hereinafter become more readily apparent have been achieved by discovering that certain pentacyclic triterpenoid compounds, including α-boswellic acid, β-boswellic acid, and acetyl α-boswellic acid, and other derivatives of these compounds, have abilities to inhibit topoisomerase I and topoisomerase II, and to induce cellular differentiation *in vitro* and, it is expected, *in vivo*. Significantly, it has been demonstrated that compositions based on these molecules have potent anti-cancer activity in tumorbearing mice. As a result, anti-cancer activity is expected in other mammals, including humans.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5 shows a gel electrophoresis analysis of topoisomerase I relaxation of DNA.

FIG. 6 shows a gel electrophoresis analysis of topoisomerase II unknotting of DNA.

DESCRIPTION OF THE PREFERRED EMBODIMENTS

The Chinese herbal medicine Tian-Shian-Wan has been reported in Chinese clinical studies to have antitumor activity. No information was available as to individual chemicals present in this complex mixture of natural materials nor as to which parts of it were responsible for the reported antitumor activity. In an attempt to confirm this activity and provide a biological and biochemical basis for the reported clinical observations, a sample of this medicine (prepared from a mixture of natural sources) was subjected to extraction and separated into fractions.

Figure 1:
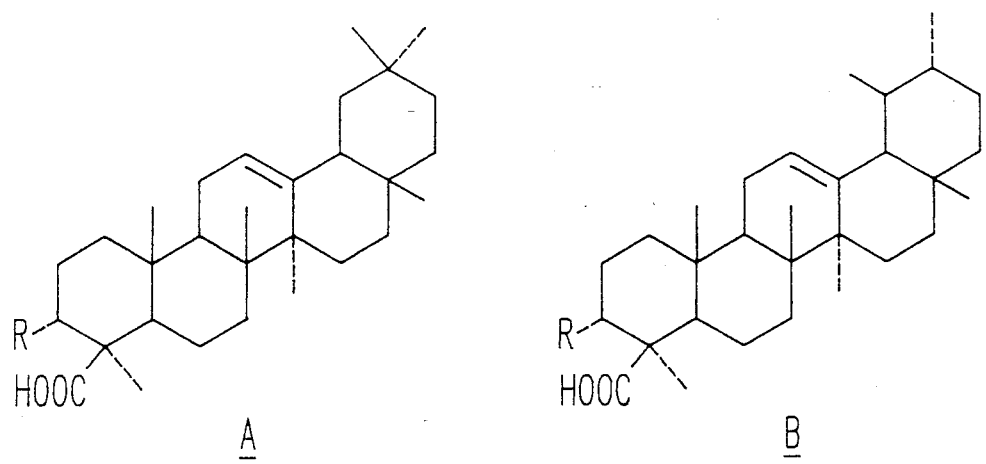
FIG. 1 shows the structures of α-boswellic acid acetate (A-1), α-boswellic acid (A-2), β-boswellic acid acetate (B-1) and β-boswellic acid (B-2).

Testing of the fractions against topoisomerase I enzyme purified from chronic human leukemic cells showed that potent inhibitory activity was present in only one of the fractions. This fraction was further purified to give a crystalline material shown by HPLC to consist of two distinct compounds. Mass spectral analysis showed the two compounds to be isomeric and gave a molecular formula $C_{32}H_{50}O_4$. From this and knowledge of the Chinese herbal medicine literature, it was possible to postulate the two compounds to be the acetates of α-and β-boswellic acid (A-1 and B-1 in FIG. 1), respectively.

Figure 4:
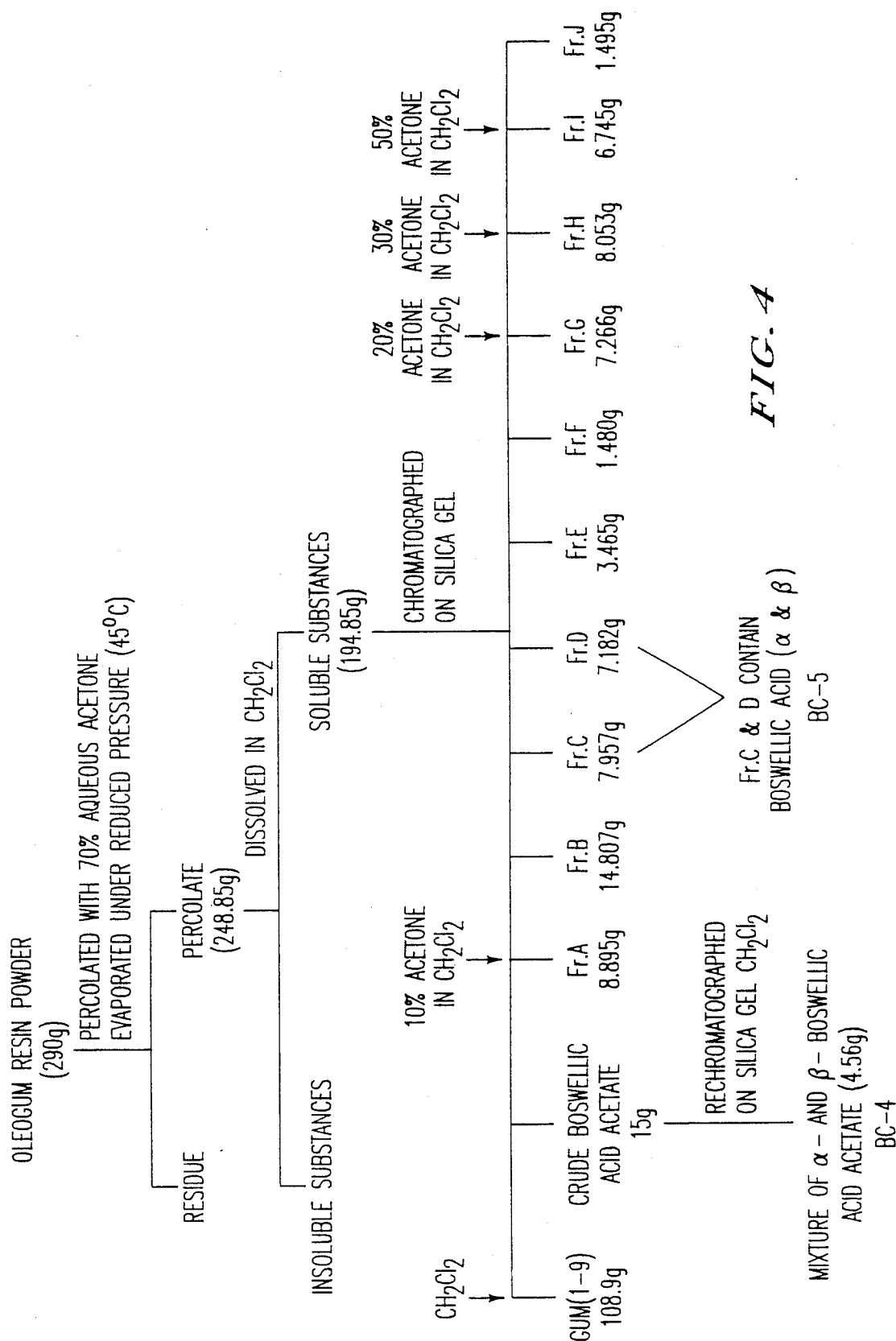
FIG. 4 shows a separation scheme of oleogum resin exudate from *Boswellia carterii Birdw*.

The exudative resin from *Boswellia carterii Birdw* containing these two compounds was then obtained, and they were isolated as shown in FIG. 4 and shown to be identical with the materials from Tian-Shian-Wan. The structures of the compounds were established by mass spectrometry, which gave the molecular formula and showed a highly characteristic retro-Diels Alder fragment in addition to other characteristic peaks. NMR spectra, including determination of two dimensional carbon-hydrogen correlation spectra and carbon-13 NMR spectra, were also in accord with the structures shown. X-ray crystalloqraphy studies have also confirmed the structure of the β-boswellic acid acetate. Moreover, 2D-NMR of α-boswellic acid acetate is in accord with structure A-1.

Both α- and β-boswellic acid acetates were tested for their ability to inhibit topoisomerase I and topoisomerase II according to the procedures of Hsiang et al. (1985). Very surprisingly in view of their nonaromatic structures, both boswellic acid acetate isomers were highly active against topoisomerase I and II (see FIGS. 5 and 6). The α-isomer A-1 is the more potent of the two forms and is more potent than the standard compound, camptothecin, in the topoisomerase I inhibition assay. The isomers A-1 and B-1 are equipotent in topoisomerase II inhibition and are more potent than the standard compound VP-16-213 (Etoposide), which shows significant clinical activity against small-cell lung cancer, testicular cancer, lymphoma and leukemia (O'Dwyer, P., et al., Etoposide (VP-16-213), Current Status of an Active Anti-cancer Drug, New Engl. J. Med. 312, 692-700 (1985)).

The study of the compounds at the Institute of Materia Medica in Beijing, PRC, has also shown that they induce differentiation in HL-60 cells at a concentration of 10 μg/ml (see Example 4).

More significantly, these *in vitro* activities are in accordance with an animal study at the Institute of Materia Medica in which four out of ten tumor (L-1210) bearing mice survived while all of the mice in the control group died (see Example 5).

As described above, the boswellic acid compounds have three hitherto unreported properties which should be of significant medical advantage. These are their inhibition of topoisomerase I, inhibition of topoisomerase II, and ability to induce cell differentiation. All three of these properties are important in anticancer drugs.

The presence and properties of topoisomerases in cells are relatively recent discoveries. In view of the extreme importance of transcription, recombination, and repair of DNA in cell growth, replication, and function, it seems likely that other possible applications of topoisomerase inhibitors may appear as more is learned about these enzymes.

The compounds of this invention differ markedly from known inhibitors of the enzymes in being nonaromatic in character. In addition, as illustrated above, they are more potent than camptothecin and VP-16. They thus represent a novel structural type which may not exhibit some of the toxic side effects of the currently known compounds. Both scientifically and practically, this is a remarkable and unexpected finding.

Thus, in accordance with the present invention, it has been discovered unexpectedly that α-boswellic acid acetate, β-boswellic acid acetate and their analogs are potent topoisomerase I and II inhibitors and are capable of induction of cell differentiation at low concentration.

This invention discloses for the first time that pentacyclic triterpenoids can exhibit strong topoisomerase I and II inhibitory activities and cell differentiation induction properties.

Figure 3:
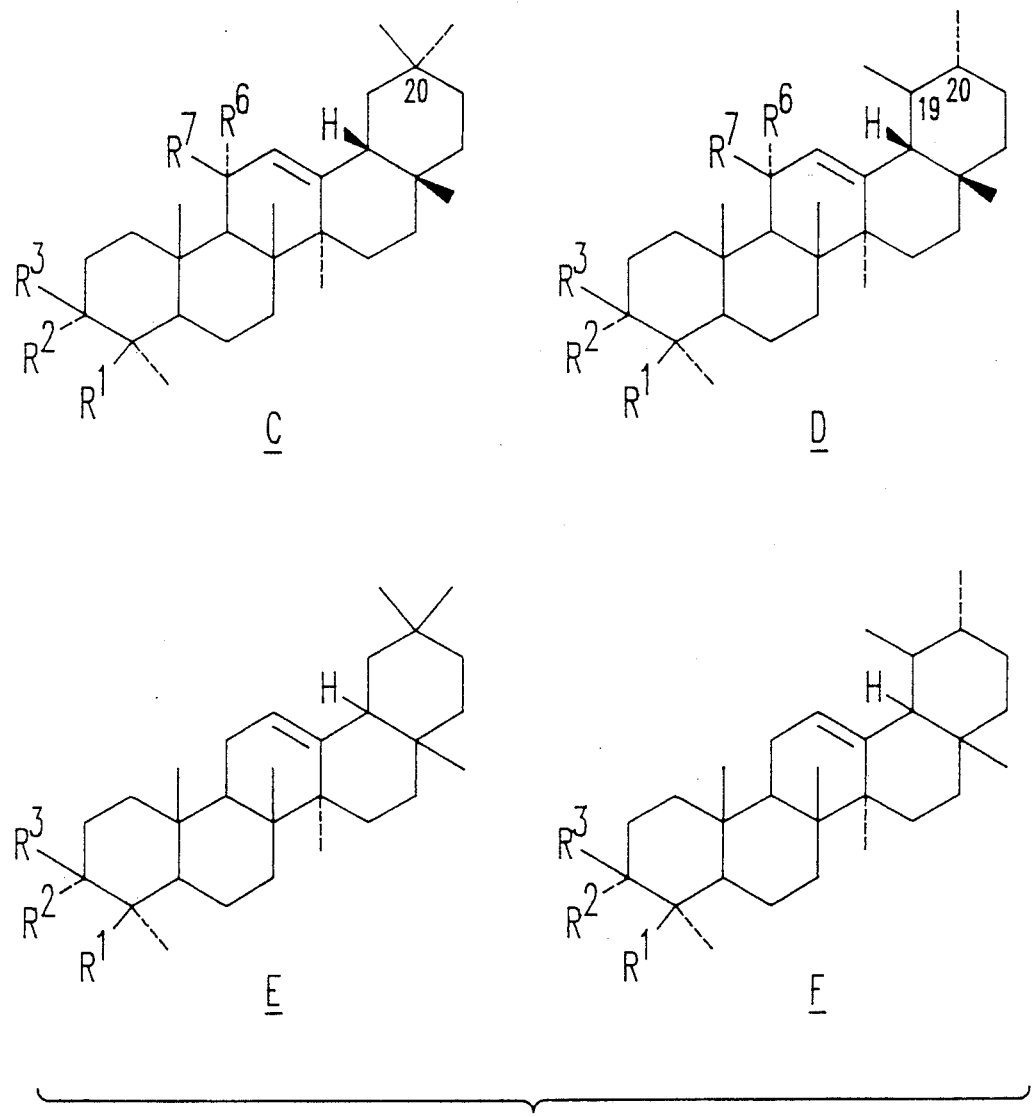
FIG. 3 shows the generic structures of triterpenoids of the present invention. $R^1$–$R^7$ are identified herein.

The triterpenoids of the present invention comprise compounds having structures C and D of FIG. 3, wherein $R^1$ is $-COOR^4$, where $R^4$ is a mono; di; or trisaccharide; -H; $C_{1-4}$ alkyl; $C_{2-4}$ alkenyl; $C_{3-4}$ alkynyl; $C_{6-8}$ aryl which is unsubstituted or is substituted by halogen, methoxy, ethoxy, sulfonamido, amino, mono- or di-$C_{1-4}$-alkyl-amino, mono- or di-acetylamino, $C_{1-4}$ alkyl, $C_{2-4}$ alkenyl; or $R^1$ is $-CONH_2$; $-CONHR^5$; where $R^5$ is a mono; di; or trisaccharide; $-CH_3$; $-CH_2COOH$; $-CH_2CH_2COOH$; $C_{2-8}$ alkyl; $C_{2-8}$ alkenyl; $C_{2-8}$ alkynyl; $C_{6-8}$ aryl which is unsubstituted or is substituted by halogen, methoxy, ethoxy, sulfonamido, amino, mono- or di-$C_{1-4}$-alkyl-amino, mono- or di-acetylamino, $C_{1-4}$ alkyl, or $C_{2-4}$ alkenyl, and $R^2$ and $R^3$ may be combinations of hydrogen or $R^5$, with -H, $-OR^4$, $-NH_2$, $-NHR^5$, $-NHR_2^{5,}$

wherein $R^4$ and $R^5$ are as defined above, or $R^2$ and $R^3$ together may be =O or =N-$OR^4$, wherein $R^4$ is as defined above, and $R^6$ and $R^7$ may be combinations of hydrogen or $R^5$, with =H, $-OR^4$, $-NH_2$, $-NHR^5$, $-NHR_2^5$,

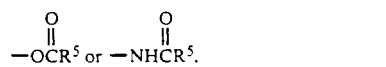

wherein $R^4$ and $R^5$ are as defined above, or $R^6$ and $R^7$ together may be =O or =N-$OR^4$, wherein $R^4$ is as defined above.

As examples of $C_{1-4}$ alkyl groups, there may be mentioned methyl, ethyl, propyl, butyl, sec-butyl, and tert-butyl. As $C_{2-8}$ alkyl, there may in addition be mentioned pentyl, hexyl, heptyl, and octyl. For $C_{2-4}$ alkenyl, there may be mentioned ethenyl, 1-propenyl, and 2-propenyl. As $C_{2-8}$ alkenyl, there may in addition, be mentioned 1-pentenyl. Analogous alkynyl groups are also contemplated.

For aryl, there may be mentioned a phenyl group or a phenyl group substituted by halogen, O-$C_{1-4}$-alkyl, sulfonamido, amino, $C_{1-4}$-alkyl amino, or acetylamino.

For mono, di or trisaccharides, there may be mentioned glucosyl, galactosyl, fructosyl, and the like.

Preferred groups for $R^1$ are -COOH, -COOCH$_3$, -COOC$_2$H$_5$ and -CONH$_2$.

Preferred groups for $R^2$ when $R^3$ is -H are -H, -OH, -OAc, -OCOC$_2$H$_5$, and -NHAc.

When $R^2$ is -H, $R^3$ is preferably -H, -OH, -OAc, -OCOC$_2$H$_5$, or -NHAc; or $R^2R^3$ is =O, =NOH, or =NOCH$_3$.

Preferred groups for $R^6$ and $R^7$ are the same as those of $R^2$ and $R^3$.

Preferred are combinations wherein $R^1$ is -COOH or -COOCH$_3$, either-$R^2$ or $R^3$ is -H and the other is -OH, -OAc, -OCOC$_2$H$_5$ or -NHAc and $R^6=R^7=$-H.

Also preferred are combinations in which $R^1$ is -COOH or -COOCH$_3$, either $R^2$ or $R^3$ is -H and the other is -OH, -OAc, -OCOC$_2$H$_5$ or -NHAc and either $R^6$ or $R^7$ is H and the other is -OH, -OAc, or -OCOC$_2$H$_5$.

Also preferred are combinations in which $R^1$ is -COOH or -COOCH$_3$, either $R^2$ or $R^3$ is -H and the other is -OH, -OAc or -OCOC$_2$H$_5$, and $R^6R^7$ is =O, =NOH or =NOCH$_3$.

Particularly preferred are combinations in which $R^1$ is -COOH or -COOCH$_3$, $R^3$ is -H and $R^2$ is -OH, -OAc or -OCOC$_2$H$_5$, and $R^6$ and $R^7$ are -H.

Most particularly preferred are combinations in which $R^1$ is -COOH, $R^2$ is -OH, -OAc or -OCOC$_2$H$_5$, and $R^3$, $R^6$ and $R^7$ are H.

As used herein, halogen, means preferably Cl, Br, I or F.

Also included within the scope of the present invention are pharmaceutically acceptable salts of salt-forming compounds falling with the scope of the above description. In particular, when an anionic group is present on the molecule, any of the well-known pharmaceutically acceptable cations may be associated therewith. Thus, for example, sodium, potassium, calcium and quaternary amine salts, including ammonium, could be employed. Preferably, sodium and potassium salts are employed. Furthermore, when a group capable of forming a cation is present on the molecule, a pharmaceutically acceptable anion may be associated therewith. Examples of such anions are acetate, aspartate, benzoate, fumarate, ethanesulfonate, hydrochloride, lactate, oxalate, tosylate, etc. Of these salts, simple inorganic salts, such as salts of the hydrogen halides are preferred.

The present invention is also directed to pro-drug compounds analogous to the active compounds disclosed herein. Such compounds are generally themselves be inactive or low in activity, but are converted in vivo into active compounds. Thus, for example, pro-drugs such as the methyl ester of any acid functionality which is not active per se or has very low activity could be hydrolyzed, either uncatalytically or catalytically with an enzyme such as an esterase, to an active compound such as boswellic acid. Such pro-drug compounds could well be the preferred therapeutic form of the present compounds. These analogous pro-drug compounds can be produced from active compounds based on procedures and factors which are well known to those of ordinary skill in the art. Accordingly, as used in the present application, "pro-drug analog" means "a chemical which is relatively non-toxic and pharmacodynamically inert but which can be transformed in vivo to a pharmacologically active drug" (Connors, T. A., Xenobiotica, 16:975 (1986)). More specifically it means a derivative or analog of the triterpenoids of the present invention which have relatively low or no ability to inhibit topoisomerase I or II or to cause cell differentiation or to kill cancer cells, until converted in the body to a derivative or analog with such ability or abilities. Such pro-drug compounds should have favorable properties such as enhanced absorption, water solubility, lower toxicity, or better targeting to the tumor cell (such as by reason of greater affinity for the tumor cell or a larger quantity of activating enzyme in the tumor cell as opposed to a normal cell so that larger concentrations of the active compound are produced in the tumor cell). Examples of such compounds are esters such as methyl, ethyl, phenyl, N,N-dimethylaminoethyl, acyl derivatives such as benzoyl, p-N,N-dimethylaminobenzoyl, N,N-dimethylaminoglycyl, peptide derivatives such as γ-glutamyl, glycyl, D-Val-Leu-Lys (cf.

Chakravarty, P. K., et al., J. Med. Chem., 26:663 (1983)), or glycoside derivatives such as glucuronides (cf. Connors, T. A. and Whisson, M., Nature 210:866 (1966)).

Standard procedures such as esterification, hydrolysis, amidation of carboxylic acids or esters or oxidation, reduction or organometallic (e.g. Grignard) reactions, lead to the substituents $R^1$, $R^2$ and $R^3$. Allylic oxidation or bromination yields compounds in which $R^6$, $R^7 =$ H, OH; H, Br; or $=$O followed by standard procedures of oxidation, reduction, esterification or nucleophilic displacement leading to the substituents $R^6$ and $R^7$. Compounds in which $R^2R^3$ or $R^6Rhu 7$ are $=$O can be converted to oximes or alkoximes by standard procedures.

The active (i.e. non-pro-drug) compounds of the present invention have $K_i$'s with topoisomerases I and II, as determined by the method of Hsiang (1985), and as exemplified in the example below, of 50 micromolar or less. Preferably, the $K_i$ will be from one nanomolar to 20 micromolar. Accordingly, as used herein. "inhibitory effective amount" of one of the present compounds means an amount of the composition sufficient to result in 50-100% inhibition of the enzyme, preferably 70-100% inhibition, as determined by an *in vitro* test using a compound having the desired $K_i$ value.

The active (i.e. non-pro-drug) compounds of the present invention have cell differentiation inducing ability in HL 60 cells, as determined by the method of Lu and Han, 1986 and exemplified in the example below, at concentrations of 100 µg per ml or less. Preferably the effective concentration will be from 1 ng to 100 µg per ml, particularly preferably from 0.1 to 50 µg per ml. As used herein, "effective amount for differentiation" of one of the present compounds means an amount of the composition sufficient to result in 25-100% cell differentiation, preferably 50-100% cell differentiation, as determined by an *in vitro* test using a compound having the desired effective cell differentiation concentration.

Compounds having inhibitory activity against either or both of topoisomerase I or topoisomerase II are covered by this invention. It will also be understood that such compounds may be used to inhibit not only the topoisomerase I and II enzymes currently known to those skilled in the art, but also may be used to inhibit other known or to be discovered isoenzymes of this type and other topoisomerase enzymes (DNA gyrases) having related activity, as will be apparent to one skilled in the art.

Likewise, the compounds of this invention may be used to induce cell differentiation in other cells than those of the present example, as will be apparent to one skilled in the art.

A compound having a structural formula as described in the present application may possess only one of the activities described herein. Such a compound is still part of the present invention. Thus, for example, a given compound may exert topoisomerase I inhibitory ability and not topoisomerase II inhibitory ability. Similarly, a compound of the present invention may induce cell differentiation but not inhibit either of the two topoisomerase enzymes. Such compounds are part of the present invention, as are compounds possessing any combination of the activities described herein.

DNA topoisomerase I was originally identified from *Escherichia coli* as a single enzyme activity capable of relaxing supercoiled DNA (Wang, 1971). Subsequently, topoisomerase I activity from many eukaryotic cells has been isolated (Champoux and Dulbecco, 1972; Dynan et al., 1981; Liu and Miller, 1981; Castora, 1986). The enzyme has no requirement for a high-energy cofactor such as ATP or AND. It acts by forming a covalent enzyme-DNA intermediate. This transient DNA break allows changes of linking number between the two strands of DNA. The topoisomerase I enzyme is a monomeric protein of approximate molecular weight 100 kDa, and relaxes both negatively and positively supercoiled DNA. It has been firmly established that, unlike the prokaryotic enzyme which binds to the 5' end, eukaryotic topoisomerase I forms a covalent intermediate with the 3' end of the broken DNA via a tyrosine residue (Gellert, 1981; Liu, 1983; Wang, 1985).

Topoisomerase II has been isolated from *E. coli* and eukaryotic organisms (Baldi, 1980; Hsieh, 1980) such as calf thymus and human HeLa cells (Liu, 1981; Glisson, 1984). Eukaryotic topoisomerase II is a homologous dimer with a molecular weight of 300 kDa (Liu et al., 1980).

The eukaryotic type II topoisomerase yields an identical cleavage site at the 5' ends (Sander, 1983).

Direct evidence that some anti-cancer drugs enhance DNA cleavage by purified eukaryotic DNA topoisomerase II has been reported (Nelson, 1984; Tewey, 1984; Ross, 1984; and Minocha, 1984).

Specific cancers which may be mentioned as susceptible to treatment by administration of compounds in accordance with the present invention include small cell lung cancer, testicular cancer, lymphoma and leukemia (based on analogous VP-16 activity); esophageal cancer, and stomach cancer; colon cancer (based on analogous activity with camptothecin); breast cancer; cancers of the central nervous system (based on likelihood that the compounds will cross the blood brain barrier); liver cancer; and prostate cancer. Other cancers may also be susceptible to treatment with these compounds, and such activity can be readily measured using standardized tests including activity against tumor implants in nude, athymic mice models, known to those of ordinary skill in the art. Cells associated with these cancers comprise examples of cells in which differentiation can be induced using compounds or compositions of the present invention.

Other compounds having topoisomerase I or topoisomerase II inhibitory activity have use in the treatment of cancer in humans and nonhuman mammals (Rose, K. M., FASEB J. 2, 2474-2478, 1988). Chemical compounds capable of modulating topoisomerase enzyme activity have considerable value for recombination of DNA in gene manipulations as well.

By non-human mammals, is meant, for example, dogs, cats, monkeys, cows, horses, etc. Although the enzymes contained in these mammals may not be exactly the same as topoisomerase I or topoisomerase II isolated from a human source, if their function is generally the same in these non-human mammals as in humans, and inhibition is detectable by a standard assay (such as those identified herein), then the inhibitory effect is within the scope of the compositions and methods of the present invention.

Some clinically effective anticancer agents such as daunorubicin or cytarabine are capable of effectively inducing the differentiation of various myeloid leukemic cells, thus compounds possessing cell differentiation induction properties have use in anticancer purposes.

The compounds of the present invention may be administered by oral, parenteral, or intravenous route, or by absorption through skin or mucous membrane surfaces using methods known to those skilled in the art of drug delivery.

For the purposes of therapeutic administration, the active ingredient may be incorporated into a solution or suspension.

The solutions or suspensions may also include the following components: a sterile diluent such as water for injection, saline solution, polyethylene glycols, glycerin, propylene glycol or other synthetic solvents; proteins such as serum albumin to enhance solubility; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The preparation can be enclosed in ampoules, disposable syringes or multiple dose vials made of glass or plastic.

site, liposomes which are preferentially adsorbed to the cancerous site, and other agents known to those of ordinary skill in the art which are preferentially attracted to or absorbed into cancerous sites. Such agents are described in, for example, Ghose, T., et al., Antibody-Linked Cytotoxic Agents in the Treatment of Cancer: Current Status and Future Prospects, J. Natl. Cancer Inst. 61 (1978). The amount of the targeting agent can be determined by one of ordinary skill in the art without undue experimentation. In general, when the targeting agent is a monoclonal antibody or another cytotoxic agent which is covalently attached to the compound according to the present invention, an approximately equimolar or less amount of the targeting agent will be utilized. However, it is also possible for different molar ratios of the present compounds and the covalently attached agents to be utilized.

Specific examples of monoclonal antibodies which might be used in accordance with the present invention and associated cancers which could be targeted by the present compounds are the following:

| Monoclonal Antibodies | | | |
|---|---|---|---|
| PRODUCT | COMPANY | INDICATION | STATUS |
| Panorex MAb | Centocor (Malvern, Pa.) | colorectal cancer, pancreatic cancer | Phase II |
| Ovarian RT MAb | Centocor (Malvern, Pa.) | ovarian cancer | Phase I |
| MAb | Cetus (Emeryville, Ca.) | breast cancer | Phase I |
| MAb | Damon (Needham Heights, Mass.) | lung cancer | Phase I |
| KS ½-DAVLB MAb | Eli Lilly (Indianapolis, Ind.) | cancer | in clinical trials |
| MAb-L6 | Bristol-Myers/ Oncogen (New York, N.Y.) | lung cancer | Phase I |
| MAb | Immunomedics (Newark, N.J.) Johnson & Johnson (New Brunswick, N.J.) | colorectal cancer | Phase I |

The compositions containing the active compounds of the present invention can be formulated so as to be specifically targeted to tumors. For example, any of the various compounds of the present invention could be covalently attached to a monoclonal antibody which is directed to a tumor-associated antigen. Such linkages could be made through peptide bond formation with amino groups of an antibody. More preferably, such linkages should contain a disulfide moiety or other readily cleayed moiety, such as is described by Vitetta et al. (E. S. Vitetta, R. Jerrold Fulton, Richard D. May, Mark Till, Jonathan W. Uhr, Science, 238:1098 (1987), designed such that the compound released by the cleavage of the disulfide link is rapidly converted to the active topoisomerase inhibitor or cell differentiation inducer. Alternatively the compounds of this invention could be attached to or incorporated into liposomes, which are known to be useful for targeting anticancer drugs (G. Gregoriadis, J. Senior and A. Trouet, Editors, Targeting of Drugs, NATO Advanced Study Institute Series, Vol. 47, Plenum Press, New York, 1982). Liver cancer is especially susceptible to liposome targeting. Procedures for the preparation and use of such liposomes are discussed in the book by Gregoriadis et al.

Hence, as used herein, agents for targeting the compounds of the present invention to cancerous sites, include monoclonal antibodies specific to the cancerous Other monoclonal antibodies could also be used, as long as they are targeted to specific cancerous sites, e.g. tumors.

Compounds of the present invention may also be administered in combination with other therapeutic treatments, such as radiation therapy for cancer, or in combination with other anticancer drugs, for example, cytotoxic drugs or other topoisomerase inhibitors or cell differentiation inducers.

While dosage values will vary with the specific severity of the cisease condition to be alleviated, good results are achieved when the compounds described herein are administered to a subject requiring such treatment as an effective oral, parenteral or intravenous dose. The appropriate dose may be estimated from the effective amount of the compounds, the described in vitro tests and the bioavailability of the compounds described by the route administered, so as to produce an effective concentration of the compounds described at the target site in the body of the subject.

It is to be understood, however, that for any particular subject, specific dosage regimens should be adjusted to the individual need in the professional judgment of the person administering or supervising the administration of the aforesaid compound. It is to be further understood that the dosages set forth do not limit the scope or practice of the invention. The dosages may be administered at once, or may be divided into a number of smaller dosages to be administered at varying intervals of time.

Other features of the invention will become apparent in the course of the following descriptions of exemplary embodiments which are given for illustration of the invention only and are not intended to be limiting thereof.

EXAMPLES

EXAMPLE 1

Isolation and Purification of α- and β-Boswellic Acid Acetate

As shown in FIG. 4, the resin (290 g) was exhaustively extracted with 70% aqueous acetone in a percolator to yield a crude extract (248.8 g, 85.7%). The crude extract was treated with methylene chloride, and the methylene chloride soluble fraction was concentrated (194.8 g, 65.1%). This crude mixture was chromatographed over silica gel by using increasing amounts of acetone in methylene chloride as the eluent.

From methylene chloride eluants, a crude mixture of α- and β-boswellic acid acetate (16 g) was obtained. After repeated chromatography and recrystallization in methanol, fine colorless needle crystals (4.54 g) were obtained. HPLC analysis indicated that the crystalline material was still a mixture, consisting of α- and β-boswellic acid acetates in an approximately 1:1 ratio.

0.25 g of the isomeric mixture was chromatographed over a C×18 reversed phase column (25 mm x 30 cm) by using 92% aqueous methanol as the mobile phase. Fractions containing pure α- and β-boswellic acid acetate (determined by HPLC analysis) were combined and concentrated, respectively. Further recrystallization from methanol provided 5 mg of α-boswellic acid acetate (A-1) and 11 mg of β-boswellic acid acetate (B-1).

Identification of α-Boswellic Acid Acetate and β-Boswellic Acid Acetate

The structures of α- and β-boswellic acid acetates were confirmed based on the following physical and spectral analysis.

α-Boswellic Acid Acetate

Colorless needles, $[\alpha]_D^{22} + 66.2°$, HRMS 498.3697, $C_{32}H_{50}O_4$, calculated 498.3709. Its IR spectrum showed carbonyl bands at 1734 $cm^{-1}$ for acetoxy and 1692 $cm^{-1}$ for the carboxyl group. The EI mass spectrum showed peaks at m/z 280, 218, which represent the characteristic retro-Diels-Alder cleavage peaks from ring-C of $\Delta^{12}$- oleanene/ursene derivatives. Its $^1$H NMR spectrum showed eight methyl signals (cf. Table I). Its $^{13}$C NMR spectrum revealed thirty-two carbon signals.

β-Boswellic Acid Acetate

Colorless needles, $[\alpha]_D^{22} + 60.0°$, HRMS 498.3701, $C_{32}H_{50}O_4$, calculated 498.3709. Its IR spectrum showed carbonyl bands at 1733 $cm^{-1}$ for acetoxy and 1693 $cm^{-1}$ for the carboxyl group. The EI mass spectrum showed the characteristic peaks as in α-boswellic acid acetate. Its $^1$H NMR spectrum also showed eight methyl signals (Table I). Its $^{13}$C NMR spectrum revealed thirty-two carbon signals.

Figure 2:
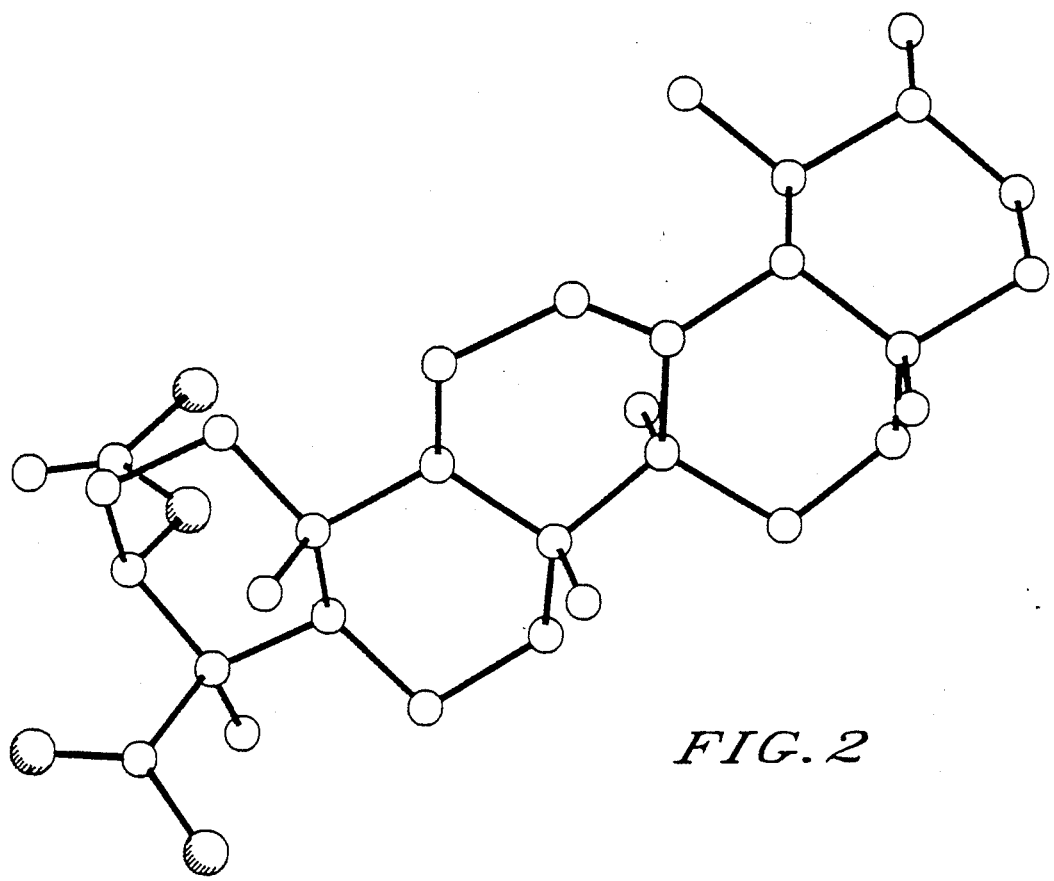
FIG. 2 shows the structure of β-boswellic acid acetate in the crystalline state as revealed by X-ray crystallography.

X-ray diffraction analysis (cf. FIG. 2) confirmed the structure of β-boswellic acid acetate.

TABLE I

| | Chemical Shift of the Me Groups (ppm from TMS) for α- and β-Boswellic Acid Acetate | | | | | | | |
|---|---|---|---|---|---|---|---|---|
| | 23 Me | 25 Me | 26 Me | 27 Me | 28 Me | 29 Me | 30 Me | —CO—$CH_3$ |
| α-Boswellic Acid Acetate | 0.90 | 1.01 | 1.19 | 1.24 | 0.84 | 0.87 | 0.87 | 2.09 |
| β-Boswellic Acid Acetate | 0.91 | 1.05 | 1.12 | 1.25 | 0.81 | 0.81 | 0.91 | 2.10 |

EXAMPLE 2

Topoisomerase I Inhibitory Activity

Topoisomerase I inhibitory activity was monitored by using the supercoiled pBR 322 DNA relaxation assay according to a published procedure [Liu et al., Proc. Natl. Acad. Sci., U.S.A., 76, 3487 (1987)].

DNA topoisomerase I was purified to homogeneity from chronic human leukemic cells. Plasmid pBR 322 DNA was purified by phenol deproteinization of cleared lysates followed by CsCl/ethidium isopycnic centrifugation and gel filtration. The topoisomerase I inhibitory activities of compounds A-1 and B-1 are summarized in FIG. 5. The α isomer A-1 showed higher potency (~3X) than standard camptothecin. The β isomer B-1 showed comparable potency to standard camptothecin.

EXAMPLE 3

Topoisomerase II Inhibitory Activity

Topoisomerase II activity was monitored by using the $P_4$ unknotting assay [Liu et al., Nucleic Acid Res., 9, 3979 (1981)]. Naturally knotted DNA isolated from the tailless capsids of a phage was used as the substrate. Topoisomerase II was purified from human leukemic cells. Both isomers A-1 and B-1 showed higher potency than standard VP-16. The results are summarized in FIG. 6.

EXAMPLE 4

Cell Differentiation Induction Activity

Cultured human promyeloid leukemia cell lines, HL-60, were induced by an approximate 1:1 ratio mixture of compounds A 1 and B-1 to differentiate into mature cells. Cell differentiation was assessed by the procedure of Lu and Han [Lu, Y. and Han, R., Differentiation of Human Promyelocytic Cells (HL-60) Induced by Aclacinomycin B, Acta Academia Medica Sinica, 8(37), 211-214 (1986)]. Duplicate cultures were carried for each of 5 culture days in the presence of the test mixture drug at various concentrations (see Table II).

TABLE II

EFFECT ON HL-60 CELLS

| Concentration (μg/ml)* | NBT Reduction %** |
|---|---|
| 1 | 2.5 |
| 8 | 27.0 |
| 10 | 51.0 |

*Mixture of A-1 and B-1 in ca. 1:1 ratio.
**Increase over control cells in ability to reduce NBT.

EXAMPLE 5

In vivo Antitumor Activity

The effect of the compounds on L-1210 leukemia was determined by administering a 1:1 mixture of α-boswellic acid acetate and β-boswellic acid acetate to CDF-1 mice. L-1210 cells ($1 \times 10^6$ cells/mouse) were implanted intraperitoneally into CDF-1 mice (10 mice/group) on day 0 and intraperitoneal treatment with the compounds was initiated on day 1 for 12 days. The results are summarized in Table III.

TABLE III

ACTION OF BC-4* ON L-1210 BEARING MICE (IN VIVO)

| Group | Animal Number Initial | Animal Number Final** | Body Weight Initial | Body Weight Final | Average Survival Time (Days) |
|---|---|---|---|---|---|
| Control | 16 | 0 | 17.0 | 19.7 | 15.7 ± 1.9 |
| 50 mg/kg | 10 | 1 | 16.9 | 17.8 | 16.9 ± 6.1 |
| 100 mg/kg | 10 | 4 | 16.7 | 17.4 | 22.9 ± 8.5 |

*BC-4 consisted of α-boswellic acid acetate and β-boswellic acid acetate in an approximately 1:1 ratio.
**Animals surviving to end of experiment (day 30).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for inhibiting topoisomerase I, which comprises contacting topoisomerase I *in vitro* or *in vivo* with an inhibitory effective amount of a compound selected from the group consisting of those having the following formulas:

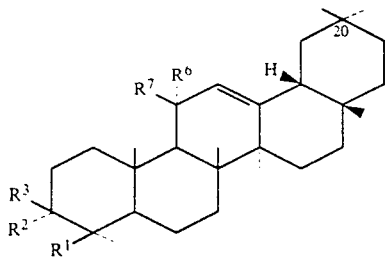

C

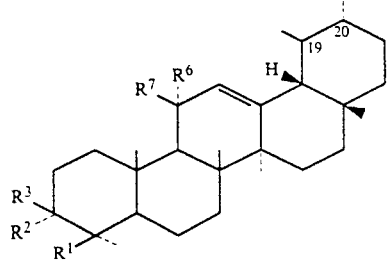

D

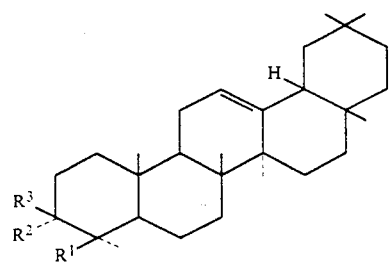

E

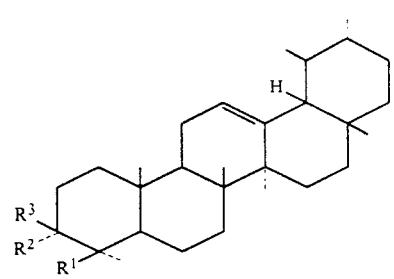

F wherein $R^1$ is -COOR$^4$, is a -H; $C_{1-4}$ alkyl; $C_{2-4}$ alkenyl; $C_{3-4}$ alkynyl; $C_6$-$C_8$ aryl which is unsubstituted or is substituted by halogen, methoxy, ethoxy, sulfonamido, amino, mono- or di-$C_{1-4}$-alkyl-amino, mono- or di-acetylamino, $C_{1-4}$ alkyl, $C_{2-4}$ alkenyl, or $R^1$ is -CONH$_2$; -CONHR$^5$; or -CONR$_2^5$, where $R^5$ is a -CH$_3$; -CH$_2$COOH; -CH$_2$CH$_2$COOH; $C_{2-8}$ alkyl; $C_{2-8}$ alkenyl; $C_{2-8}$ alkynyl; or $C_{6-8}$ aryl which is unsubstituted or is substituted by halogen, methoxy, ethoxy, sulfonamido, amino, mono- or di-$C_{1-4}$-alkyl-amino, mono- or di-acetylamino, $C_{1-4}$ alkyl, $C_{2-4}$ alkenyl, and $R^2$ and $R^3$ may be combinations of hydrogen or $R^5$, with -H, -OR$^4$, -NH$_2$, -NHR$^5$, -NHR$_2^5$,

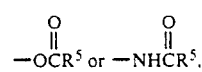

wherein $R^4$ and $R^5$ are as defined above, or
$R^2$ and $R^3$ together may be =O or =N-OR$^4$, wherein $R^4$ is as defined above, and
$R^6$ and $R^7$ may be combinations of hydrogen or $R^5$, with -H, -OR$^4$, -NH$_2$, -NHR$^5$, -NHR$_2^5$,

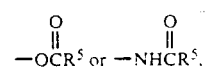

wherein $R^4$ and $R^5$ are as defined above, or
$R^6$ and $R^7$ together may be =O or =N-OR$^4$, wherein $R^4$ is as defined above, and
pharmaceutically acceptable salts thereof.

2. The method according to claim 1, wherein $R^1$ is -COOR$^4$, wherein $R^4$ is -H, $C_{1-4}$ alkyl, or $NH_2$.

3. The method according to claim 1, wherein $R^3$ is -H and $R^2$ is -H, -OH, -OAc, -OCOC$_2$H$_5$ or -NHAc.

4. The method of claim 1, wherein $R^6=R^7=R^3=H$, $R^2=OH$, and $R^1=COOH$.

5. The method of claim 1, wherein $R^6=R^7=R^3=H$, $R^2=OCOCH_3$, and $R^1=COOH$.

6. The method of claim 1, wherein $R^6=R^7=R^3=H$, $R^2=OH$, and $R^1=COOH$.

7. A method for inhibiting topoisomerase II, which comprises contacting topoisomerase II *in vitro* or *in vivo* with an inhibitory effective amount of a compound selected from the group consisting of those having the following formulas:

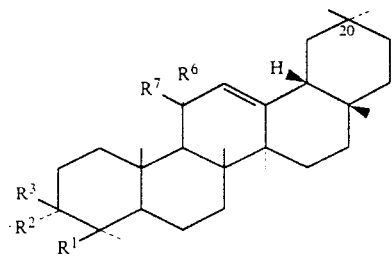
C

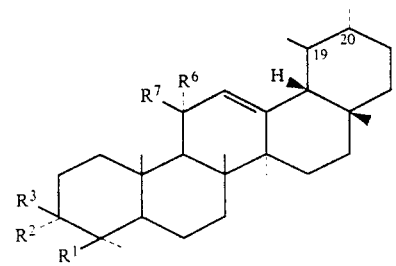
D

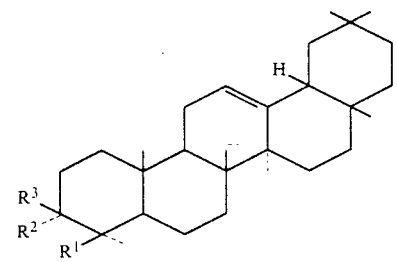
E

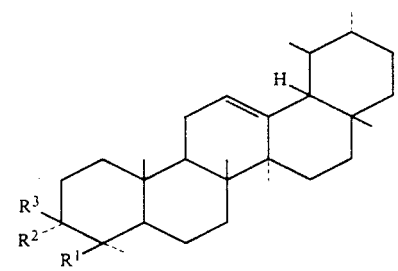
F wherein $R^1$ is -COOR$^4$, where $R^4$ is a -H; $C_{1-4}$ alkyl; $C_{2-4}$ alkenyl; $C_{3-4}$ alkynyl; $C_6$-$C_8$ aryl which is unsubstituted or is substituted by halogen, methoxy, ethoxy, sulfonamido, amino, mono- or di-$C_{1-4}$-alkyl-amino, mono- or diacetylamino, $C_{1-4}$ alkyl, $C_{2-4}$ alkenyl, or $R^1$ is -CONH$_2$; -CONHR$^5$; or -CONR$_2^5$, where $R^5$ is a -CH$_3$; -CH$_2$COOH; -CH$_2$CH$_2$COOH; $C_{2-8}$ alkyl; $C_{2-8}$ alkenyl; $C_{2-8}$ alkynyl; $C_{6-8}$ aryl which is unsubstituted or is substituted by halogen, methoxy, ethoxy, sulfonamido, amino, mono- or di-$C_{1-4}$-alkyl-amino, mono- or di-acetylamino, $C_{1-4}$ alkyl, $C_{2-4}$ alkenyl, and $R^2$ and $R^3$ may be combinations of hydrogen or $R^5$, with -H, -OR$^4$, -NH$_2$, -NHR$^5$, -NHR$_2^5$,

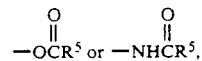

wherein $R^4$ and $R^5$ are as defined above, or $R^2$ and $R^3$ together may be =O or =N-OR$^4$, wherein $R^4$ is as defined above, and $R^6$ and $R^7$ may be combinations of hydrogen or $R^5$, with -H, -OR$^4$, -NH$_2$, -NHR$^5$, -NHR$_2^5$,

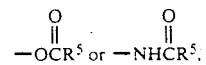

wherein $R^4$ and $R^5$ are as defined above, or $R^6$ and $R^7$ together may be =O or =N-OR$^4$, wherein $R^4$ is as defined above, and pharmaceutically acceptable salts thereof.

8. The method according to claim 7, wherein $R^1$ is -COOR$^4$, wherein $R^4$ is -H, $C_{1-4}$ alkyl, or $NH_2$.

9. The method according to claim 7, wherein $R^3$ is -H, and $R^2$ is -H, -OH, -OAc, -OCOC$_2$H$_5$ or -NHAc.

10. The method of claim 7, wherein $R^6=R^7=R^3=H$, $R^2=OH$, and $R^1=COOH$.

11. The method of claim 7, wherein $R^6=R^7=R^3=H$, $R^2=OCOCH_3$, and $R^1=COOH$.

12. A composition for treatment of a mammal suffering from a cancer selected from the group consisting of small cell lung cancer, testicular cancer, lymphoma, leukemia, esophageal cancer, stomach cancer, colon cancer, breast cancer, central nervous system cancer, liver cancer and prostate cancer, which comprises:

a compound selected from the group consisting of those having the following formulas:

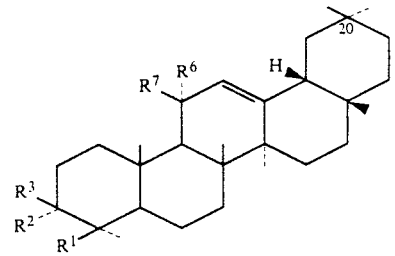
C

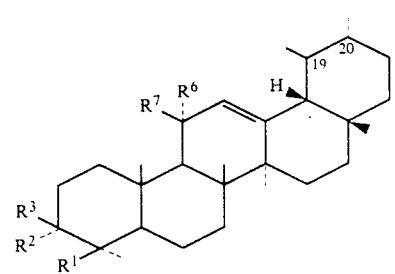
D

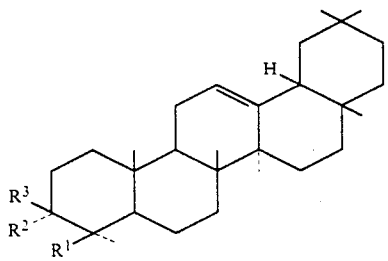
E

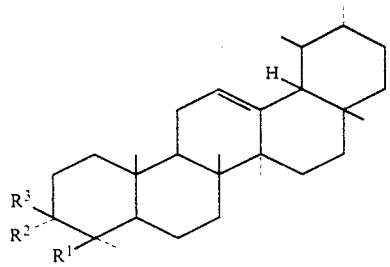
F

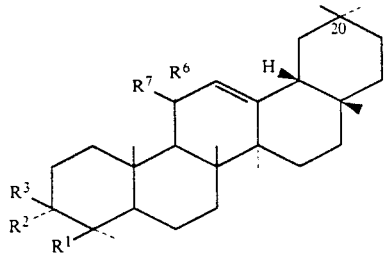
C

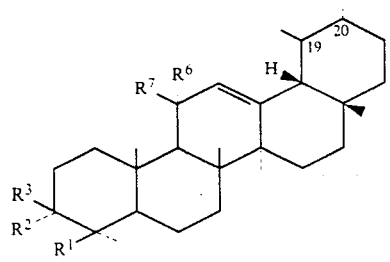
D

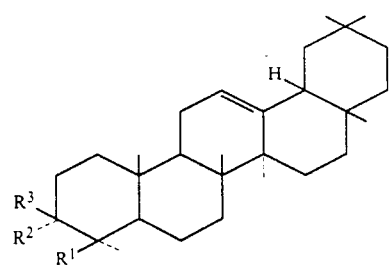
E

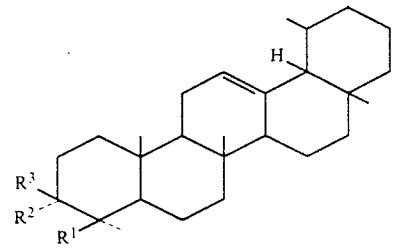
F wherein $R^1$ is -COOR$^4$, where $R^4$ is a -H; $C_{1-4}$ alkyl; $C_{2-4}$ alkenyl; $C_{3-4}$ alkynyl; $C_6$-$C_8$ aryl-which is unsubstituted or is substituted by halogen, methoxy, ethoxy, sulfonamido, amino, mono- or di-$C_{1-4}$-alkyl-amino, mono- or diacetylamino, $C_{1-4}$ alkyl, or $C_{2-4}$ alkenyl, or $R^1$ is -CONH$_2$; -CONHR$_5$; or -CONR$_2{}^5$ where $R^5$ is a -CH$_3$; -CH$_2$COOH; -CH$_2$CH$_2$COOH; $C_{2-8}$ alkyl; $C_{2-8}$ alkenyl; $C_{2-8}$ alkynyl; or $C_{6-8}$ aryl which is unsubstituted or is substituted by halogen, methoxy, ethoxy, sulfonamido, amino, mono- or di-$C_{1-4}$-alkyl-amino, mono- or di-acetylamino, $C_{1-4}$ alkyl, $C_{2-4}$ alkenyl, and $R^2$ and $R^3$ may be combinations of hydrogen or $R^5$, with -H, -OR$^4$, -NH$_2$, -NHR$^5$, -NHR$_2{}^5$,

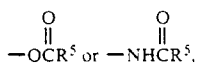

wherein $R^4$ and $R^5$ are as defined above, or $R^2$ and $R^3$ together may be =O or =N-OR$^4$, wherein $R^4$ is as defined above, and $R^6$ and $R^7$ may be combinations of hydrogen or $R^5$, with -H, -OR$^4$, -NH$_2$, -NHR$^5$, -NHR$_2{}^5$,

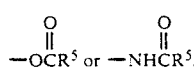

wherein $R^4$ and $R^5$ are as defined above, or $R^6$ and $R^7$ together may be =O or =N-OR$^4$, wherein $R^4$ is as defined above, and pharmaceutically acceptable salts thereof, in combination with an agent for targeting said compound to the site where said cancer is localized in said mammal.

13. A method for inducing cellular differentiation, which comprises contacting a cancerous cell with an effective amount of a compound selected from the group consisting of those having the following formulas:

wherein Rhu 1 is -COOR$^4$, where $R^4$ is a -H; $C_{1-4}$ alkyl; $C_{2-4}$ alkenyl; $C_{3-4}$ alkynyl; $C_{6-8}$ aryl which is unsubstituted or is substituted by halogen, methoxy, ethoxy, sulfonamido, amino, mono- or di-$C_{1-4}$-alkyl-amino, mono- or diacetylamino, $C_{1-4}$ alkyl, $C_{2-4}$ alkenyl, or $R^1$ is -CONH$_2$; -CONHR$^5$; or -CONR$_2{}^5$, where $R^5$ is a -CH$_3$; -CH$_2$COOH; -CH$_2$CH$_2$COOH; $C_{2-8}$ alkyl; $C_{2-8}$ alkenyl; $C_{2-8}$ alkynyl; or $C_{6-8}$ aryl which is unsubstituted or is substituted by halogen, methoxy, ethoxy, sulfonamido, amino, mono- or di-$C_{1-4}$-alkyl-amino, mono- or di-acetylamino, $C_{1-4}$ alkyl, $C_{2-4}$ alkenyl, and $R^2$ and $R^3$ may be combinations of hydrogen or $R^5$, with -H, -OR$^4$, -NH$_2$, -NHR$_2{}^5$,

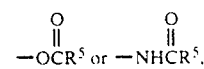

wherein $R^4$ and $R^5$ are as defined above, or $R^2$ and $R^3$ together may be $=O$ or $=N\text{-}OR^4$, wherein $R^4$ is as defined above, and $R^6$ and $R^7$ may be combinations of hydrogen or $R^5$, with -H, -OR$^4$, -NH$_2$, -NHR$^5$, -NHR$_2^5$,

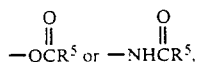

wherein $R^4$ and $R^5$ are as defined above, or $R^6$ and $R^7$ together may be $=O$ or $=N\text{-}OR^4$, wherein $R^4$ is as defined above, and pharmaceutically acceptable salts thereof.

14. A method of treating a cancer selected from the group consisting of small cell lung cancer, testicular cancer, lymphoma, leukemia, esophageal cancer, stomach cancer, colon cancer, breast cancer, central nervous system cancer, liver cancer and prostate cancer, which comprises administering to a mammal in need thereof an effective amount of a composition containing as the active ingredient therein a compound selected from the group consisting of those having the following formulas:

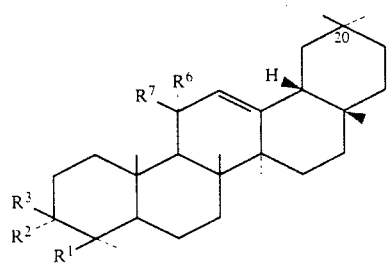

C

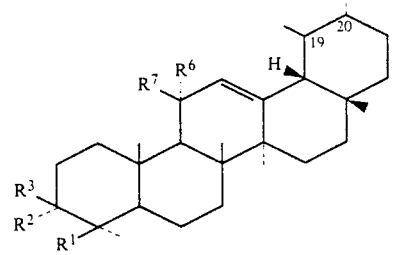

D

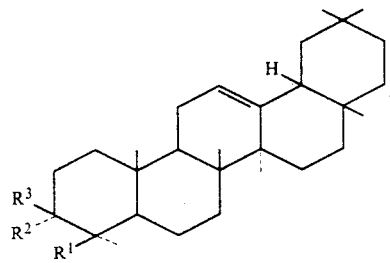

E

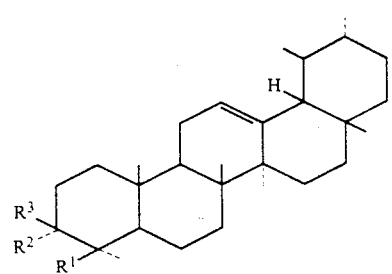

F wherein Rhu 1 is -COOR$^4$, where $R^4$ is a -H; $C_{1\text{-}4}$ alkyl; $C_{2\text{-}4}$ alkenyl; $C_{3\text{-}4}$ alkynyl; $C_6$-$C_8$ aryl which is unsubstituted or is substituted by halogen, methoxy, ethoxy, sulfonamido, amino, mono- or di-$C_{1\text{-}4}$-alkyl-amino, mono- or diacetylamino, $C_{1\text{-}4}$ alkyl, $C_{2\text{-}4}$ alkenyl, or $R^1$ -CONH$_2$; -CONR$^5$; or -CONR$_2$ $^5$, where $R^5$ is a -CH$_3$; -CH$_2$COOH; -CH$_2$CH$_2$COOH; $C_{2\text{-}8}$ alkyl; $C_{2\text{-}8}$ alkenyl; $C_{2\text{-}8}$ alkynyl; or $C_{6\text{-}8}$ aryl which is unsubstituted or is substituted by halogen, methoxy, ethoxy, sulfonamido, amino, mono- or di-$C_{1\text{-}4}$-alkyl-amino, mono- or di-acetylamino, $C_{1\text{-}4}$ alkyl, $C_{2\text{-}4}$ alkenyl, and $R^2$ and $R^3$ may be combinations of hydrogen or $R^5$, with -H, -OR$^4$, -NH$_2$, -NHR$^5$, -NHR$_2^5$,

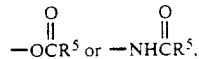

wherein $R^4$ and $R^5$ are as defined above, or $R^2$ and $R^3$ together may be $=O$ or $=N\text{-}OR^4$, wherein $R^4$ is as defined above, and $R^6$ and $R^7$ may be combinations of hydrogen or $R^5$, with -H, -OR$^4$, -NH$_2$, -NHR$^5$, -NHR$_2^5$,

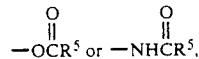

wherein $R^4$ and $R^5$ are as defined above, or $R^6$ and $R^7$ together may be $=O$ or $=N\text{-}OR^4$, wherein $R^4$ is as defined above, and pharmaceutically acceptable salts thereof.

* * * * *

UNITED STATES PATENT AND TRADEMARK OFFICE
CERTIFICATE OF CORRECTION

PATENT NO. : 5,064,823

DATED : November 12, 1991

INVENTOR(S) : Lee et al.

It is certified that error appears in the above-identified patent and that said Letters Patent is hereby corrected as shown below:

On the title page, item [75], in the address of the inventor Qi-Cheng Fang; "Beijing, Taiwan" should read --Beijing, China--.

in the addresses of the inventors Zhen-Guo Wang and De-Hua Li, "both of Jilin, Taiwan", should read --both of Jilin, China--.

in the address of the inventor C.E. Cook, "Research Trinagle Park, N.C.", should read --Research Triangle Park, N.C.--

In the abstract, line 1, "such as α boswelic", should read --such as α boswellic--.

Column 3, line 6, "TEPOISOMERASE", should read --TOPOISOMERASE--.

Column 9, line 13, "or $R^6$Rhu 7are =O", should read --or $R^6R^7$ are =O--.

Column 11, line 50, "readily cleayed", should read --readily cleaved--.

Column 13, line 43, "over a C X 18", should read --over a C-18--.

UNITED STATES PATENT AND TRADEMARK OFFICE
CERTIFICATE OF CORRECTION

PATENT NO. : 5,064,823

DATED : November 12, 1991

INVENTOR(S) : Lee et al.

It is certified that error appears in the above-indentified patent and that said Letters Patent is hereby corrected as shown below:

Column 16, line 36, "wherein $R^1$ is -COOR$^4$, is a", should read --wherein $R^1$ is -COOR$^4$, where $R^4$ is a--.

Column 20, line 48, "wherein Rhu 1 is -COOR$^4$,", should read --wherein $R^1$ is -COOR$^4$,--.

Column 22, line 25, "wherein Rhu 1 is", should read --wherein $R^1$ is--.

Signed and Sealed this

Third Day of August, 1993

Attest:

MICHAEL K. KIRK

*Attesting Officer*  *Acting Commissioner of Patents and Trademarks*